(12) United States Patent
Pederson

(10) Patent No.: US 11,989,974 B2
(45) Date of Patent: *May 21, 2024

(54) THERAPEUTIC SMILE DETECTION SYSTEMS

(71) Applicant: David K. Pederson, Mulino, OR (US)

(72) Inventor: David K. Pederson, Mulino, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/082,866

(22) Filed: Dec. 16, 2022

(65) Prior Publication Data

US 2023/0123819 A1    Apr. 20, 2023

Related U.S. Application Data

(63) Continuation of application No. 16/859,727, filed on Apr. 27, 2020.

(51) Int. Cl.
| | | |
|---|---|---|
| *G06V 40/16* | (2022.01) | |
| *A61B 5/00* | (2006.01) | |
| *A61B 5/021* | (2006.01) | |
| *A61B 5/16* | (2006.01) | |

(52) U.S. Cl.
CPC .......... *G06V 40/174* (2022.01); *A61B 5/0022* (2013.01); *A61B 5/0077* (2013.01); *A61B 5/021* (2013.01); *A61B 5/165* (2013.01); *A61B 5/4848* (2013.01); *A61B 5/681* (2013.01); *A61B 5/6898* (2013.01); *G06V 40/166* (2022.01); *G06V 40/172* (2022.01)

(58) Field of Classification Search
CPC .. G06V 40/174; G06V 40/166; G06V 40/172; G06V 40/175; A61B 5/0022; A61B 5/0077; A61B 5/021; A61B 5/165; A61B 5/4848; A61B 5/681; A61B 5/6898; A61B 5/486

See application file for complete search history.

(56) References Cited

U.S. PATENT DOCUMENTS

| | | | |
|---|---|---|---|
| 7,319,780 | B2 | 1/2008 | Fedorovskaya |
| 11,113,813 | B2 | 9/2021 | Alsan |
| 11,568,680 | B2 * | 1/2023 | Pederson ............. A61B 5/6898 |
| 2017/0286754 | A1 | 10/2017 | Eder |
| 2017/0308742 | A1 | 10/2017 | Yao |
| 2019/0208115 | A1 | 7/2019 | Paul |
| 2019/0294868 | A1 | 9/2019 | Martinez |

* cited by examiner

*Primary Examiner* — Seung H Lee

(57) ABSTRACT

Systems for detecting when a person exhibits a smile with therapeutic benefits including a facial expression detection device and a system processor. The facial expression detection device is configured to acquire facial expression data. The system processor is in data communication with the facial expression detection device and is configured to execute stored computer executable system instructions. The computer executable system instructions include the steps of receiving facial expression parameter data establishing target facial expression criteria, receiving current facial expression data from the facial expression detection device, comparing the current facial expression data to the target facial expression criteria of the facial expression parameter data, and identifying whether the current facial expression data satisfies the target facial expression criteria. The target facial expression criteria define a smile with therapeutic benefits.

20 Claims, 6 Drawing Sheets

THERAPEUTIC SMILE DETECTION SYSTEMS

PRIORITY CLAIM

This application claims priority to copending U.S. application Ser. No. 16/859,727, filed on Apr. 27, 2020, entitled Therapeutic Smile Detection Systems, which is hereby incorporated by reference in its entirety for all purposes.

BACKGROUND

Smiling is known to non-verbally communicate emotions, like happiness and joy, and other messages, such as approval between people. Lesser known is the fact that smiling can provide health benefits, both to the person observing another smiling and to the person smiling. This document will focus on the therapeutic health benefits from smiling to the person who is smiling.

Genuine smiling, often called a Duchenne smile, is a particular manner of smiling that has distinct health benefits. A genuine smile improves mood, reduces blood pressure, reduces stress, reduces pain, strengthens the immune system, strengthens relationships, increases attractiveness, and improves longevity. A genuine smile is characterized by activating muscles near the eyes and cheeks in contrast to a fake or perfunctory smile that merely involves shaping the lips.

Conventional facial recognition systems are capable of detecting certain expressions on a person's face, but are not designed to detect genuine smiles. Further, existing facial recognition systems do not include features to train people how to execute a genuine smile. Conventional facial recognition systems also lack features to encourage people to execute a genuine smile with a given frequency, for a given amount of time, and/or in response to a physiological trigger.

Thus, there exists a need for smile detection systems that improve upon and advance the design of known facial recognition systems. Examples of new and useful smile detection systems relevant to the needs existing in the field are discussed below.

SUMMARY

The present disclosure is directed to systems for detecting when a person exhibits a smile with therapeutic benefits including a facial expression detection device and a system processor. The facial expression detection device is configured to acquire facial expression data. The system processor is in data communication with the facial expression detection device and is configured to execute stored computer executable system instructions. The computer executable system instructions include the steps of receiving facial expression parameter data establishing target facial expression criteria, receiving current facial expression data from the facial expression detection device, comparing the current facial expression data to the target facial expression criteria of the facial expression parameter data, and identifying whether the current facial expression data satisfies the target facial expression criteria. The target facial expression criteria define a smile with therapeutic benefits.

DETAILED DESCRIPTION

Figure 1:
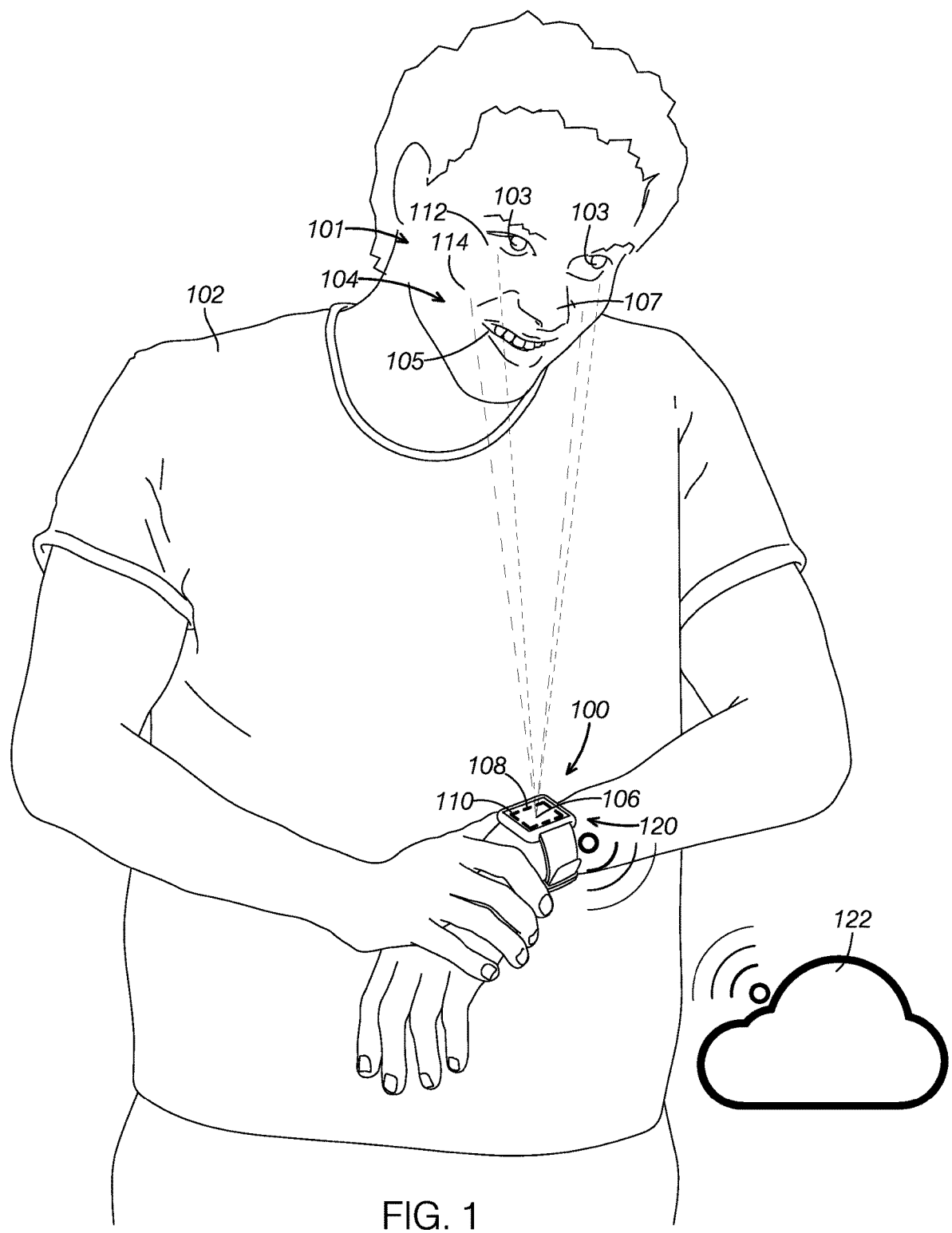
FIG. 1 is a perspective view of a system for detecting when a person exhibits a smile with therapeutic benefits incorporated into a watch on a person's wrist.

The disclosed smile detection systems will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various smile detection systems are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Definitions

The following definitions apply herein, unless otherwise indicated.

"Substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional elements or method steps not expressly recited.

Terms such as "first", "second", and "third" are used to distinguish or identify various members of a group, or the like, and are not intended to denote a serial, chronological, or numerical limitation.

"Coupled" means connected, either permanently or releasably, whether directly or indirectly through intervening components.

Therapeutic Smile Detection Systems

With reference to the figures, therapeutic smile detection systems will now be described. The systems discussed herein function to detect when a user is executing a genuine smile, also known as a Duchenne smile. The systems described in this document also function to train a user to execute a genuine smile. Another function of the systems described herein is to encourage people to execute a genuine smile to promote associated therapeutic benefits and to help establish healthy habits.

The reader will appreciate from the figures and description below that the presently disclosed systems address many of the shortcomings of conventional smile detection systems. For example, the systems described herein are sophisticated enough to detect genuine smiles in contrast to conventional facial recognition systems, which can detect only certain general expressions on a person's face. Further, the presently disclosed systems train people how to execute a genuine smile to enable them to experience the health benefits of genuine smiles. The systems discussed in this document improve over conventional facial recognition systems by encouraging people to execute a genuine smile with a given frequency, for a given amount of time, and or in response to a physiological trigger.

Contextual Details

Ancillary features relevant to the smile detections described herein will first be described to provide context and to aid the discussion of the smile detection systems.

Person

Figure 7:
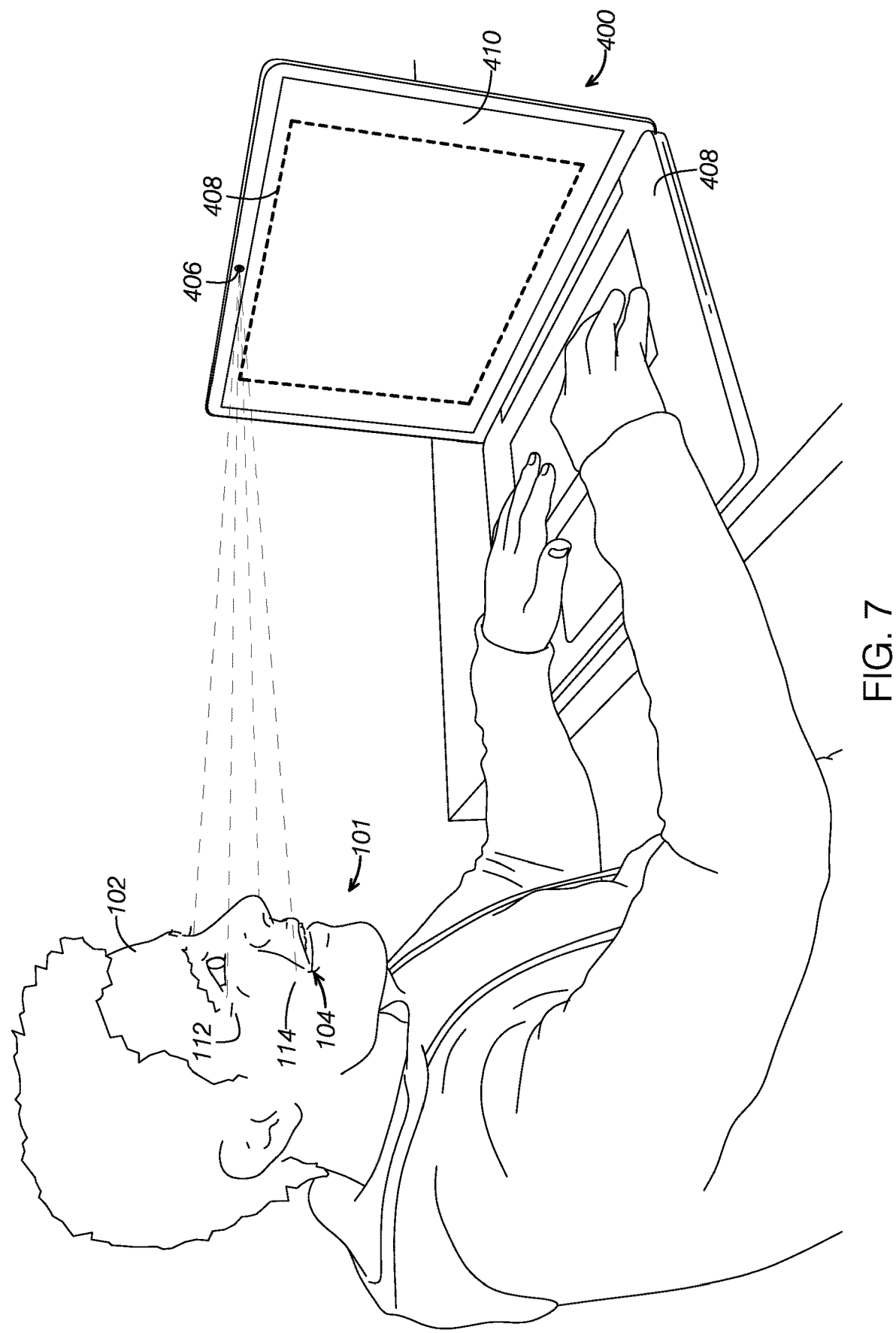
FIG. 7 is a perspective view of a third example of a system for detecting when a person exhibits a smile with therapeutic benefits incorporated into a computer with a camera.

The smile detection systems described herein function to detect a smile and other facial expressions of a person, which may also be referred to as a user. With reference to FIGS. 1 and 7, a person 102 is depicted using smile detection system 100 in FIG. 1 and using smile detection system 400 in FIG. 7. Person 102 includes a face 101, eyes 103, a mouth 105, and a nose 107. Further, person 102 includes orbicularis oculi muscles 112 near eyes 103 and zygomatic major muscles 114 near mouth 105. As shown in FIGS. 1 and 7, person 102 may exhibit a smile 104.

Smile Detection System Embodiment One

With reference to FIGS. 1-5, a first example of a smile detection system, smile detection system 100, will now be described. Smile detection system 100 includes a facial expression detection device 106, a system processor 108, and a display 110. In some examples, the smile detection system does not include one or more features included in smile detection system 100. For example, some smile detection system examples do not include a display. In other examples, the smile detection system includes additional or alternative features.

Facial Expression Detection Device

Facial expression detection device 106 is configured to acquire facial expression data.

The facial expression data may include information about the position of facial features, such as the eyes 103, nose 107, mouth 105, and ears of person 102. The facial expression data may be more granular, such as the position of specific facial muscles, such as the zygomatic major muscles 114 and/or the orbicularis oculi muscles 112 of person 102. The facial expression data may include information related to how facial features have moved by comparing the position of a given feature over time.

Additionally or alternatively to information about particular facial features, the facial expression data may include information about expressions the person is exhibiting. The expression a person is exhibiting may be determined by combining information about facial features and/or by associating expressions with defined indicators. For example, wrinkles near a person's eyes or upturned lips may be defined as indicators for a smile.

Figure 2:
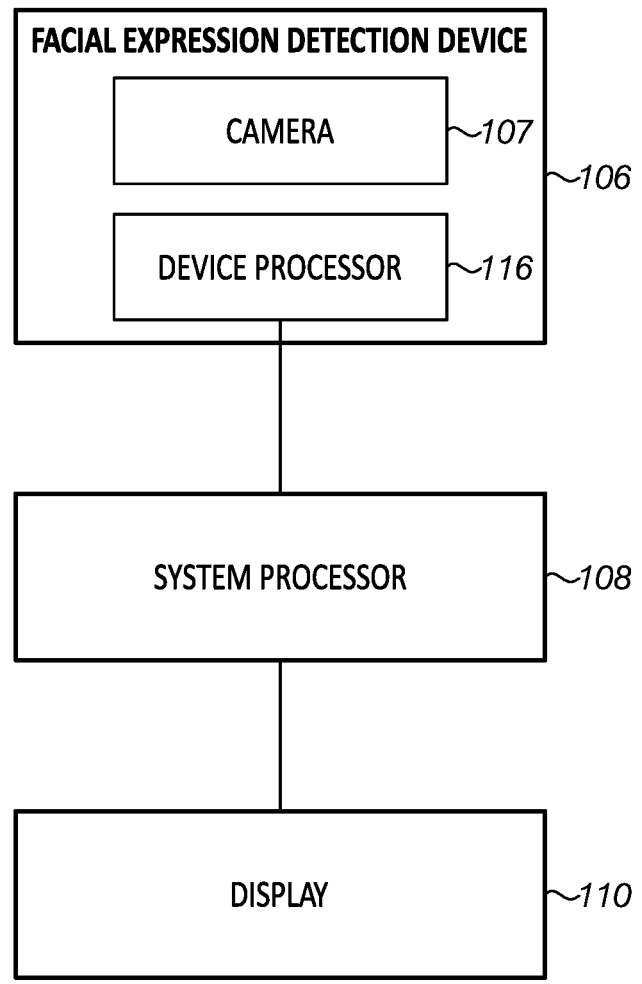
FIG. 2 is a schematic view of the system shown in FIG. 1.

As can be seen in FIGS. 1 and 2, facial expression detection device 106 includes a camera 107 and a device processor 116. Camera 107 is configured to collect facial expression data from person 102.

The camera may be any currently know or later developed camera suitable for collecting facial expression data from a person. In the example shown in FIG. 1, camera 107 is incorporated into a watch 120. In the example shown in FIG. 6, the camera is incorporated into a smartphone 220. In the example shown in FIG. 7, the camera is incorporated into a laptop computer 420.

Device processor 116 is configured to execute stored computer executable facial recognition instructions. The device processor may be any currently known or later developed processor suitable for executing computer executable instructions. The facial recognition instructions may be customized for detecting smiles with the facial expression detection device or may be more generally applicable facial recognition instructions.

Figure 6:
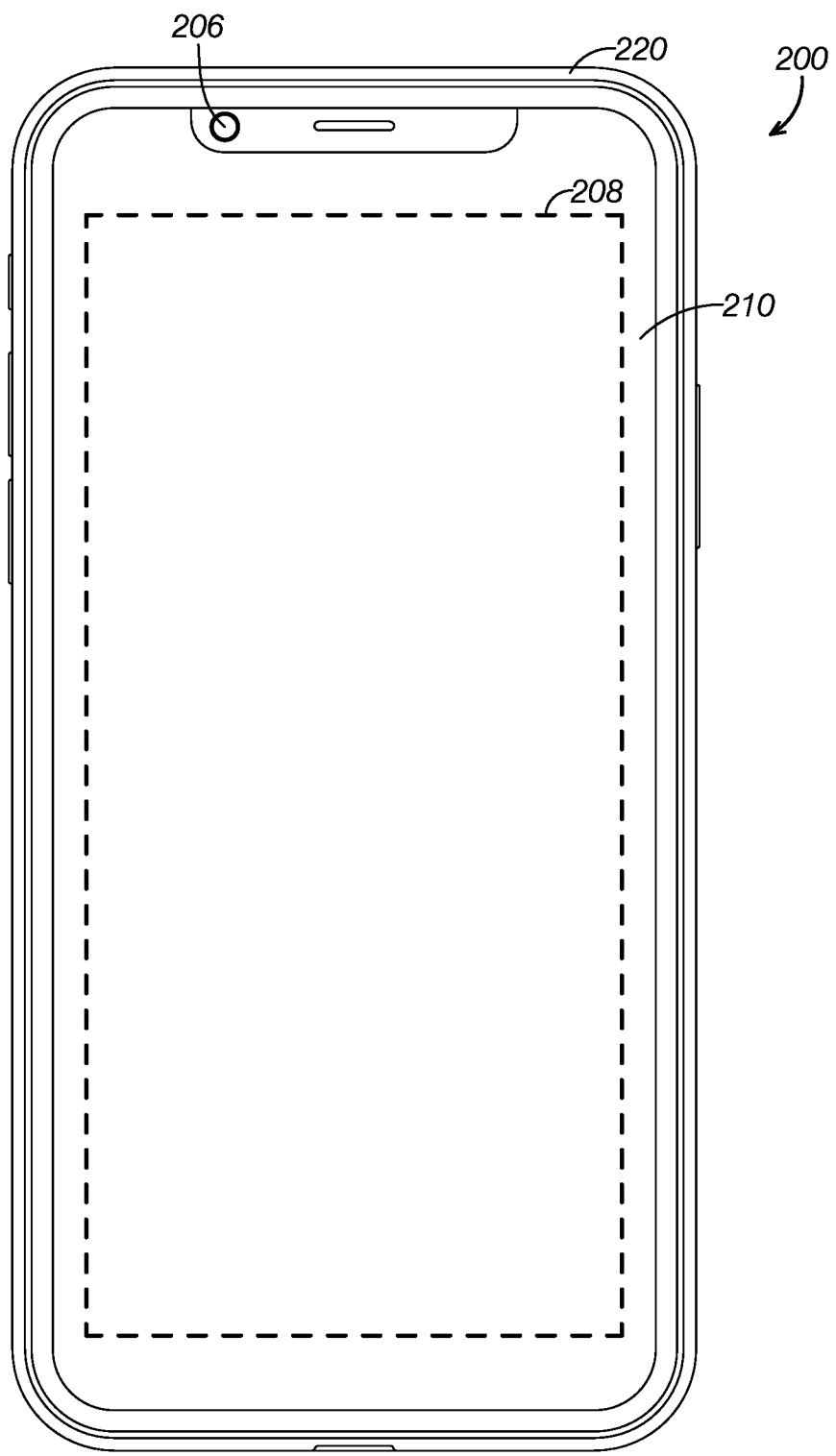
FIG. 6 is front view of a second example of a system for detecting when a person exhibits a smile with therapeutic benefits, the system incorporated into a smart phone.

As can be seen in FIG. 1, facial expression detection device 106 is incorporated into a watch 120. In particular, watch 120 is a smart watch with various computing features. However, the watch may be a traditional watch without computing features beyond the facial expression detection device. FIG. 6 depicts an example where a facial expression detection device 206 is incorporated into a handheld computing device in the form of a smartphone 220. FIG. 7 depicts an example where a facial expression detection device 406 is incorporated into a personal computing device in the form of a laptop computer 420.

System Processor

System processor 108 is configured to execute stored computer executable system instructions 300. As shown in FIG. 2, system processor is in data communication with facial expression detection device 106 and with display 110.

The system processor may be any currently known or later developed processor suitable for executing computer executable instructions. The system instructions may include instructions customized for detecting a smile 104 with facial expression detection device 106, such as system instructions 300, and more generally applicable facial recognition instructions.

Computer Executable System Instructions

Figure 3:
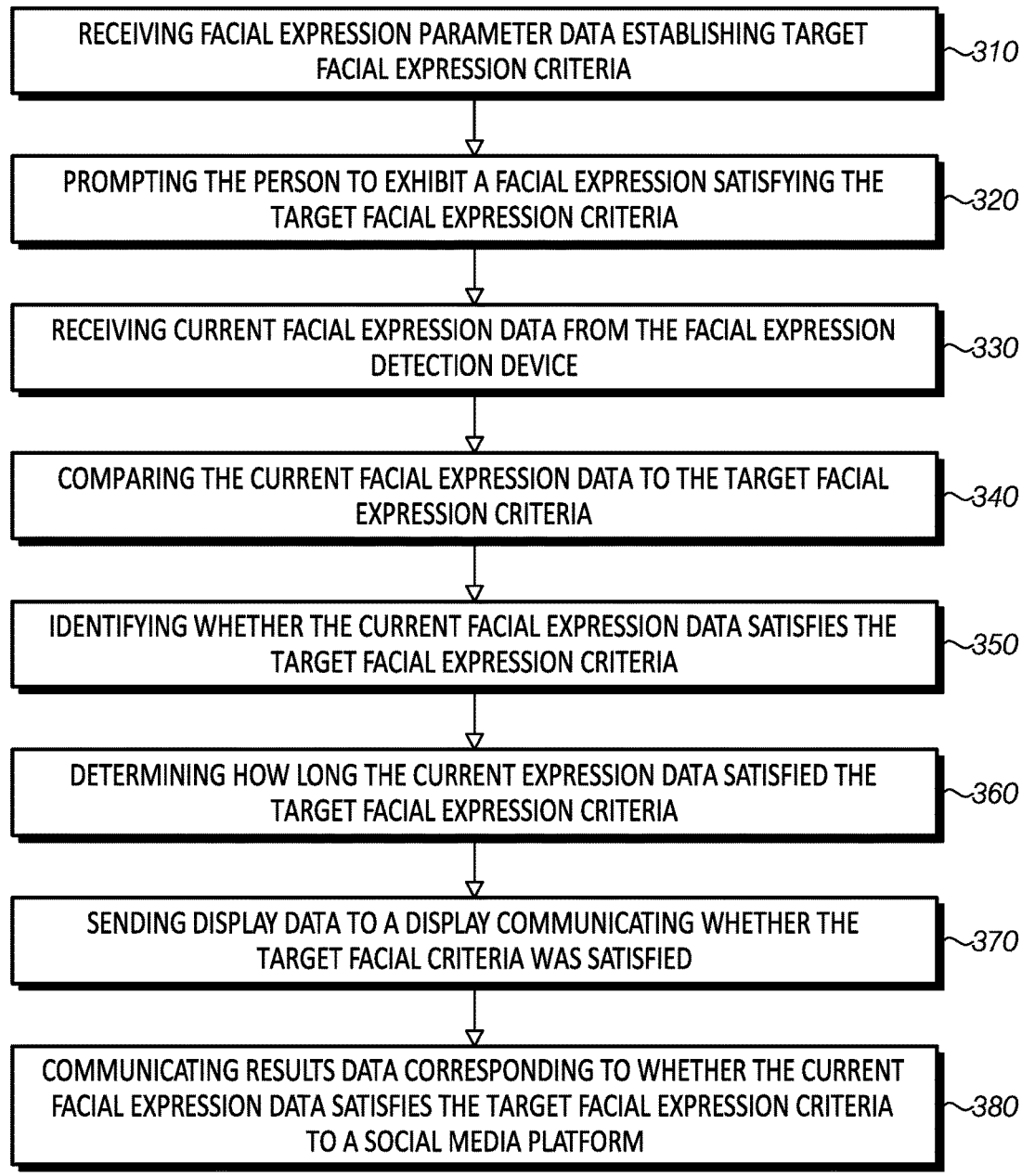
FIG. 3 is a flow diagram of computer executable instruction steps that the system shown in FIG. 1 is programmed to follow.
Figure 4:
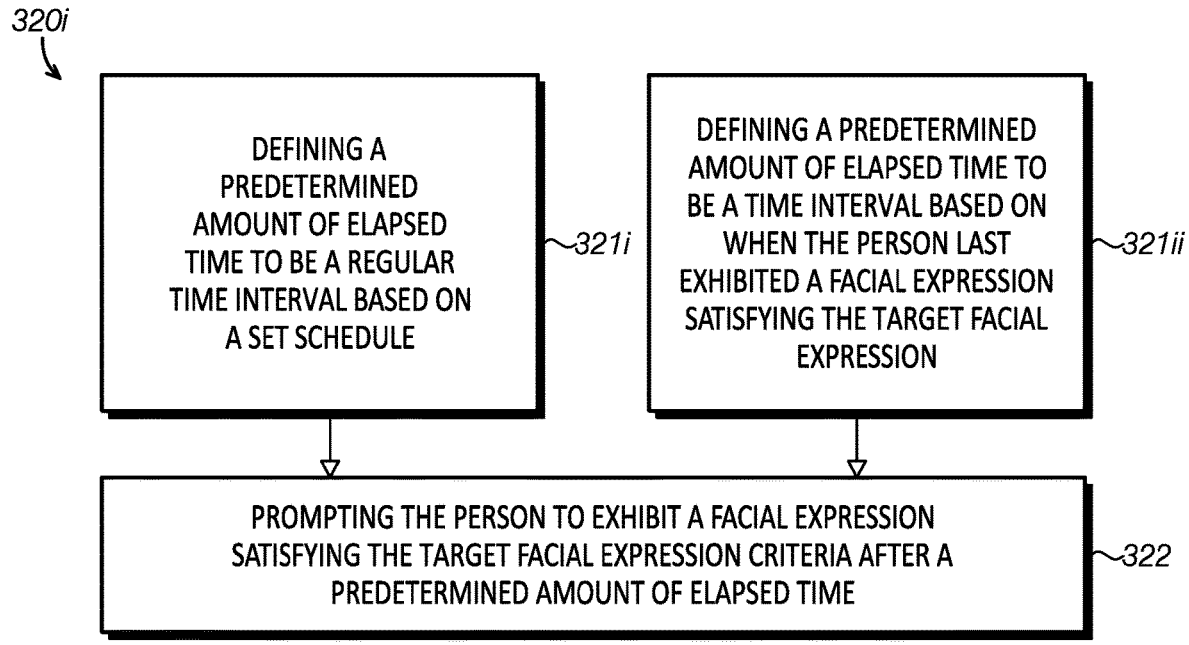
FIG. 4 is a flow diagram showing additional computer executable instruction steps associated with the step of prompting the person to exhibit a facial expression.
Figure 5:
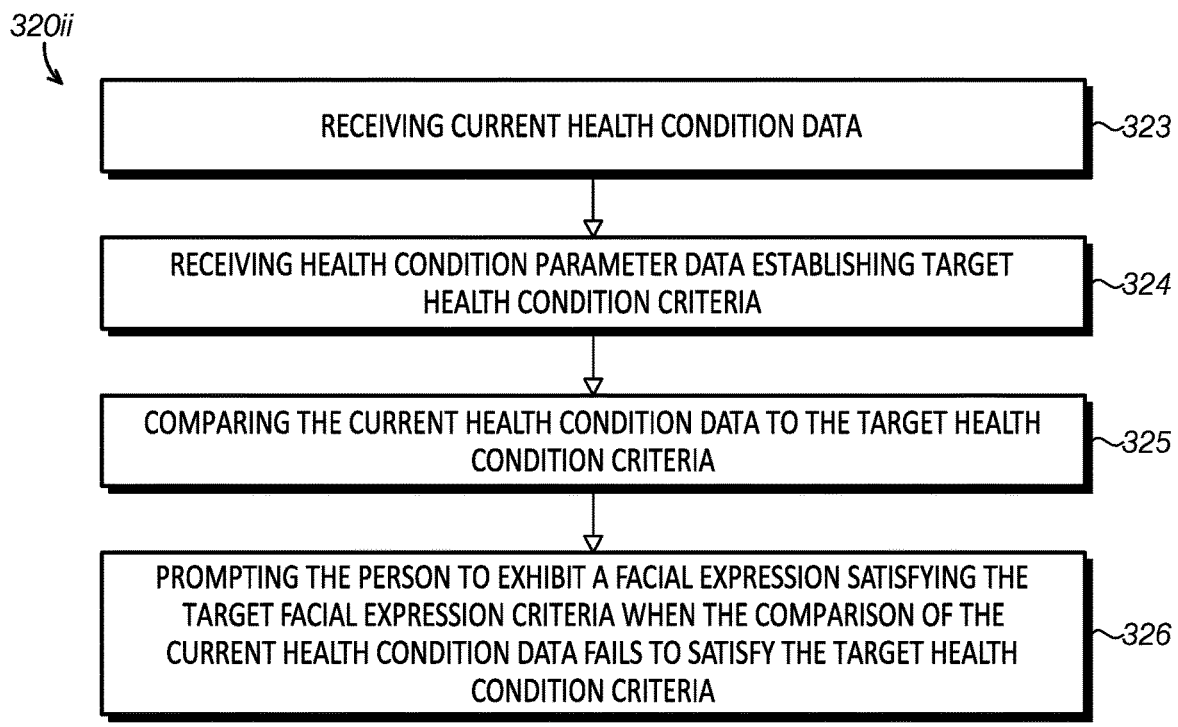
FIG. 5 is a flow diagram showing alternative additional computer executable instruction steps associated with the step of prompting the person to exhibit a facial expression.

With reference to FIGS. 3-5, a particular set of computer executable system instructions, system instructions 300, will be described. The reader should appreciate that additional or alternative system instructions may be used in different examples.

As shown in FIG. 3, system instructions 300 include the step of receiving facial expression parameter data establishing target facial expression criteria at step 310. The target facial expression criteria define a smile with therapeutic benefits. Examples of smiles with therapeutic benefits include a genuine smile, which is also known as a Duchenne smile.

The target facial expression criteria may define a smile with therapeutic benefits as occurring when zygomatic major muscles 114 of person 102 contract to a selected extent. Additionally or alternatively, the target facial expression criteria may define a smile with therapeutic benefits as occurring when orbicularis oculi muscles 112 of person 102 contract to a selected extent.

As can be seen in FIG. 3, system instructions 300 include prompting person 102 to exhibit a facial expression satisfying the target facial expression criteria at step 320. FIG. 4 depicts one example of prompting a person to exhibit a facial expression at step 320*i*. FIG. 5 depicts another example of prompting a person to exhibit a facial expression at step 320*ii*.

Prompting a person to exhibit a facial expression at step 320 may occur after a predetermined amount of elapsed time, such as shown at steps 321*i* and 321*ii* of step variation 320*i* in FIG. 4. Additionally or alternatively, prompting a person to exhibit a facial expression at step 320 may occur when a comparison of current health condition data fails to satisfy target health condition criteria, such as shown at step 326 of step variation 320*ii* in FIG. 5.

With reference to FIG. 4, the reader can see additional steps involved with prompting person 102 to exhibit a facial expression satisfying the target facial expression criteria in step variation 320*i*. Step 321*i* includes defining a predetermined amount of elapsed time to be a regular time interval based on a set schedule. Additionally or alternatively to step 321*i*, step 321ii includes defining a predetermined amount of elapsed time to be a time interval based on when person 102 last exhibited a facial expression satisfying the target facial criteria. Step variation 320i includes prompting person 102 to exhibit a facial expression satisfying the target facial expression criteria after a predetermined amount of elapsed time at step 322.

With reference to FIG. 5, the reader can see that prompting person 102 to exhibit a facial expression satisfying the target facial expression criteria in step variation 320*ii* includes receiving current health condition data at step 323. In the step 320*ii* example, the current health condition data corresponds to the health of person. The current health condition data may include blood pressure data, body temperature data, pulse rate data, metabolic data, and various other types of physiological data. In certain examples, the current health condition data includes the current facial expression data, such as whether person 102 is smiling, scowling, frowning, or tensing facial muscles.

At step 324, prompting a person to exhibit a facial expression at step 320*ii* further includes receiving health condition parameter data establishing target health condition criteria. The target health condition criteria may define conditions corresponding to low stress or other healthy states of being. The target health condition criteria may include defined ranges for blood pressure, body temperature, pulse rate, metabolic rates, and various other types of physiological parameters. The defined ranges may be selected to correspond to ranges known to promote healthy lifestyles.

In the example shown in FIG. 5, prompting a person to exhibit a facial expression at step 320*ii* also includes comparing the current health condition data to the target health condition criteria of the health condition parameter data at step 325. The comparison performed at step 325 may be used to track a user's health metrics. Additionally or alternatively, the comparison performed at step 325 may be used to trigger prompts to exhibit a facial expression.

For example, step 326 includes prompting person 102 to exhibit a facial expression satisfying the target facial expression criteria when the comparison of the current health condition data fails to satisfy the target health condition criteria. In some examples, the user is prompted to exhibit a desired facial expression immediately when the current health condition data fails to satisfy the target health condition criteria. In some examples, the user is prompted to exhibit a desired facial expression when the current health condition data fails to satisfy the target health condition criteria for a predetermined amount of time.

Returning focus to FIG. 3, system instructions 300 include receiving current facial expression data from facial expression detection device 106 at step 330. The current facial expression data may be received via a wired or wireless data connection.

At step 340, system instructions 300 include comparing the current facial expression data to the target facial expression criteria of the facial expression parameter data. After comparing the facial expression data to the target facial expression criteria at step 340, system instructions 300 include identifying whether the current facial expression data satisfies the target facial expression criteria at step 350.

In the present example, system instructions 300 include optional step 360 of determining how long the current expression data satisfied the target facial expression criteria. Other examples do not include tracking how long the target facial expression criteria was satisfied. In applications where maintaining a facial expression for a prescribed length of time is desired, such as maintaining a genuine smile for a given length of time to provide desired health benefits, tracking how long the target facial expression criteria was satisfied can assist with encouraging a user to maintain the facial expression for the prescribed time. Tracking how long the target facial expression criteria was satisfied can also help with communicating or reporting facial expression performance results.

At step 370, system instructions 300 include sending display data to display 110. The display data may communicate whether, how often, and/or for how long the target facial criteria was satisfied. The display data may also include health information, such as health benefits resulting from exhibiting facial expressions satisfying the target facial criteria.

Sending the display data to display 110 may assist the user to understand his or her facial expression performance and to make adjustments accordingly. In some examples, sending the display data to a display is performed as part of a game or contest where a user is encouraged to exhibit a desired facial expression. For example, a user may be assigned points, be awarded virtual prizes, or progress to new places in a virtual world when meeting facial expression parameters communicated to the user in the form of a game or entertainment experience.

At step 380 in FIG. 3, the reader can see that system instructions 300 include communicating results data to a social media platform, such as social media platform 122 depicted conceptually in FIG. 1. The results data may correspond to whether the current facial expression data satisfies the target facial expression criteria. Additionally or alternatively, the results data may include how often, and/or for how long the target facial criteria was satisfied. In some examples, the results data may also include health information, such as health benefits resulting from exhibiting facial expressions satisfying the target facial criteria. In examples where the system instructions incorporate or work in conjunction with a game, the results data may include the points, virtual prizes, or progress the user has achieved in the game that utilizes facial expressions.

Display

Display 110 functions to display display data to person 102. As shown in FIG. 2, display 110 is in data communication with system processor 108. Display 110 and system processor 108 may communicate data via a wired or wireless connection.

The display may be any currently known or later developed type of display for displaying data. In the example shown in FIG. 3, display 110 is a watch screen. In the example shown in FIG. 6, display 210 is a smartphone screen. In the example shown in FIG. 7, display 410 is a laptop computer screen.

Additional Embodiments

The discussion will now focus on additional smile detection system embodiments.

The additional embodiments include many similar or identical features to smile detection system 100. Thus, for the sake of brevity, each feature of the additional embodiments below will not be redundantly explained. Rather, key distinctions between the additional embodiments and smile detection system 100 will be described in detail and the reader should reference the discussion above for features substantially similar between the different smile detection system examples.

Second Embodiment

Turning attention to FIG. 6, a second example of a smile detection system, smile detection system 200, will now be described. As can be seen in FIG. 6, smile detection system 200 includes a facial expression detection device 206, a system processor 208, and a display 210. A distinction between smile detection system 200 and smile detection system 100 is that smile detection system 200 is incorporated into a smart phone 220 rather than into watch 120.

Third Embodiment

Turning attention to FIG. 7, a third example of a smile detection system, smile detection system 400, will now be described. As can be seen in FIG. 7, smile detection system 400 includes a facial expression detection device 406, a system processor 408, and a display 410. A distinction between smile detection system 400 and smile detection system 100 is that smile detection system 400 is incorporated into a laptop computer 420 rather than into watch 120.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. A system for detecting when a person exhibits a smile with therapeutic benefits, comprising:
    a display that presents a prompt to the person to exhibit a Duchenne smile;
    a facial expression detection device configured to acquire facial expression data;
    a system processor in data communication with the facial expression detection device and configured to execute stored computer executable system instructions, the computer executable system instructions including the steps of:
        receiving facial expression parameter data establishing target facial expression criteria associated with a Duchenne smile;
        receiving current facial expression data corresponding to the facial expression of the person from the facial expression detection device;
        comparing the current facial expression data to the target facial expression criteria of the facial expression parameter data; and
        identifying whether the current facial expression data satisfies the target facial expression criteria;
    wherein the target facial expression criteria define a Duchenne smile with therapeutic benefits.

2. The system of claim 1, wherein the computer executable system instructions further comprise determining a time of smile corresponding to how long the current expression data satisfied the target facial expression criteria.

3. The system of claim 2, wherein the computer executable system instructions sends display data to the display communicating the time of smile to the person.

4. The system of claim 2, wherein the computer executable system instructions further comprise:
    receiving current health condition data corresponding to the health of the person during the time of smile;
    receiving health condition parameter data establishing target health condition criteria; and
    comparing the current health condition data while the person is exhibiting their Duchenne smile to the target health condition criteria of the health condition parameter data.

5. The system of claim 4, wherein the computer executable system instructions sends display data to the display communicating to the person whether the current health condition data satisfied target health condition criteria of the health condition parameter data.

6. The system of claim 1, wherein the computer executable system instructions sends display data to the display communicating to the person whether the target facial criteria was satisfied.

7. The system of claim 1, wherein the target facial expression criteria includes:
    the zygomatic major muscles of the person contracting to a selected extent; and
    the orbicularis oculi muscles of the person contracting to a selected extent.

8. The system of claim 1, wherein the facial expression detection device includes a camera.

9. The system of claim 1, wherein the facial expression detection device is incorporated into a handheld computing device.

10. The system of claim 1, wherein the facial expression detection device is incorporated into a watch.

11. The system of claim 1, wherein the computer executable system instructions further comprise communicating results data corresponding to whether the current facial expression data satisfies the target facial expression criteria to a social media platform.

12. The system of claim 11, wherein the predetermined amount of elapsed time is a time interval based on when the person last exhibited a facial expression satisfying the target facial expression.

13. The system of claim 1, wherein the computer executable system instructions further comprise prompting the person to exhibit a facial expression satisfying the target facial expression criteria after a predetermined amount of elapsed time.

14. The system of claim 13, wherein the predetermined amount of elapsed time is a regular time interval based on a set schedule.

15. The system of claim 1, wherein the computer executable system instructions further comprise:
  receiving current health condition data corresponding to the health of the person while they are exhibiting their Duchenne smile;
  receiving health condition parameter data establishing target health condition criteria;
  comparing the current health condition data while the person is exhibiting their Duchenne smile to the target health condition criteria of the health condition parameter data; and
  re-prompting the person to exhibit a facial expression satisfying the target facial expression criteria when the comparison of the current health condition data fails to satisfy the target health condition criteria.

16. The system of claim 15, wherein the current health condition data includes blood pressure data.

17. A system for detecting when a person exhibits a smile with therapeutic benefits, comprising:
  a facial expression detection device configured to acquire facial expression data;
  a system processor in data communication with the facial expression detection device and configured to execute stored computer executable system instructions, the computer executable system instructions including the steps of:
    receiving facial expression parameter data establishing target facial expression criteria associated with a Duchenne smile;
    receiving current facial expression data corresponding to the facial expression of the person from the facial expression detection device;
    comparing the current facial expression data to the target facial expression criteria of the facial expression parameter data;
    identifying whether the current facial expression data satisfies the target facial expression criteria; and
    determining a time of smile corresponding to how long the current expression data satisfied the target facial expression criteria.

18. The system of claim 17, wherein the computer executable system instructions sends display data to a display communicating the time of smile to the person.

19. A method for detecting when a person exhibits a smile with therapeutic benefits, comprising:
  communicating a prompt to a display being viewed by the person, wherein the prompt prompts the person to exhibit a Duchenne smile;
  acquiring current facial expression data of the person corresponding to the facial expression of the person with a camera in response to communicating the prompt;
  receiving facial expression parameter data establishing target facial expression criteria associated with a Duchenne smile;
  comparing the current facial expression data to the target facial expression criteria of the facial expression parameter data; and
  identifying whether the current facial expression data satisfies the target facial expression criteria,
  wherein the target facial expression criteria define a Duchenne smile with therapeutic benefits.

20. The method of claim 19, further comprising:
  receiving current health condition data corresponding to the health of the person while they are exhibiting their Duchenne smile;
  receiving health condition parameter data establishing target health condition criteria;
  comparing the current health condition data while the person is exhibiting their Duchenne smile to the target health condition criteria of the health condition parameter data; and
  re-prompting the person to exhibit a facial expression satisfying the target facial expression criteria when the comparison of the current health condition data fails to satisfy the target health condition criteria.

* * * * *